United States Patent [19]

Prasad et al.

[11] Patent Number: 5,668,272
[45] Date of Patent: Sep. 16, 1997

[54] METHOD FOR PRODUCING SYNTHETIC N-LINKED GLYCOCONJUGATES

[75] Inventors: A. V. Krishna Prasad, Ottawa; James C. Richards, Nepean, both of Canada

[73] Assignee: National Research Council of Canada, Ottawa, Canada

[21] Appl. No.: 496,975

[22] Filed: Jun. 30, 1995

[51] Int. Cl.$^6$ .............................. C07H 5/04; C07H 5/06; C07K 9/00
[52] U.S. Cl. .................. 536/55.3; 536/55.2; 530/322
[58] Field of Search .................. 536/55.2, 55.3; 530/322

[56] References Cited

U.S. PATENT DOCUMENTS

| 5,019,231 | 5/1991 | Bradley et al. .................. 536/127 |
| 5,212,298 | 5/1993 | Rademacher et al. .................. 536/55.2 |
| 5,280,113 | 1/1994 | Rademacher et al. .................. 536/55.3 |

FOREIGN PATENT DOCUMENTS

| 413675 | 2/1991 | European Pat. Off. . |
| 538230 | 4/1993 | European Pat. Off. . |
| 2206691 | 1/1989 | United Kingdom . |
| 9209568 | 6/1992 | WIPO . |
| 9428008 | 12/1994 | WIPO . |

OTHER PUBLICATIONS

*Int. J. Peptide Res.*, vol. 39, Issued 1992, L. Varga–Defferdarovic, "Glycoconjugates of Opioid Peptides", pp. 12–17.
Bioconjugate Chem., vol. 6, 1995, pp. 316–318, D. Vetter and M.A. Gallop: "Strategies for the Synthesis and Screening of Glycoconjugates".

J. Org. Chem., vol. 23, 1958, pp. 1309–1319, H.S. Isbell and H.L. Frush: "Mutarotation, Hydrolysis, and Rearrangement Reactions of Glycosylamines".

Carbohydr. Res., vol. 149, 1986. pp. 329–345, A. Gomez–Sanchez et al: "Synthesis and Glycosidation of 1–Deoxy–1–((2,2–Diacylvinyl)amino)–D–Fructoses".

*Primary Examiner*—John Kight
*Assistant Examiner*—Everett White
*Attorney, Agent, or Firm*—J. Wayne Anderson

[57] ABSTRACT

A transamination reaction of glycosyl-1-amine with a nucleophilic reagent containing an —NH$_2$ or —NHNH$_2$ group is used to prepared a broad spectrum of glycoconjugates by substitution of the 1-amino group. The substitution reaction does not adversely affect the ring structure of the sugar as does the prior art reductive amination reaction. Suitable nucleophilic reagents are nucleophiles having a chromophore group, a fluorophore group, a chemiluminescent group, a lipid, an amino acid or peptide moiety, biotin, a drug and a linker/spacer group and an affinity label. The ratio of glycosyl-1-amine to nucleophilic reagent is in the range of from about 1:1 to about 1:2 by weight.

23 Claims, 16 Drawing Sheets

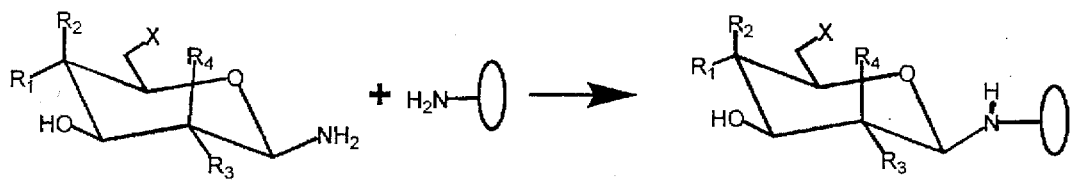
SUGAR    REAGENT
(-○)
8. $R_1, R_4 = H; R_2, R_3, X = OH$
   (1-Amino-1-deoxygalactose)
9. $R_1, R_4, X = OH; R_2, R_3 = H$
   (1-Amino-1-deoxymannose)
10. $R_1, R_4, X = H; R_2, R_3 = OH$
    (1-Amino-1-deoxyfucose)
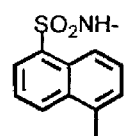
Dansyl hydrazine
11. $R_1, R_3, X = OH$
    $R_3 = NHAc$
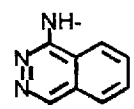
1-Hydrazinophthalazine
12. $R_1, R_3, X = OH$
    $R_3 = NHAc$
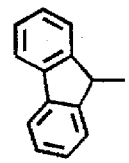
9-Fluorenamine
13. $R_1, R_3, X = OH$
    $R_3 = NHAc$
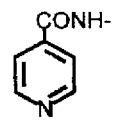
Isonicotinic hydrazide
Figure 2

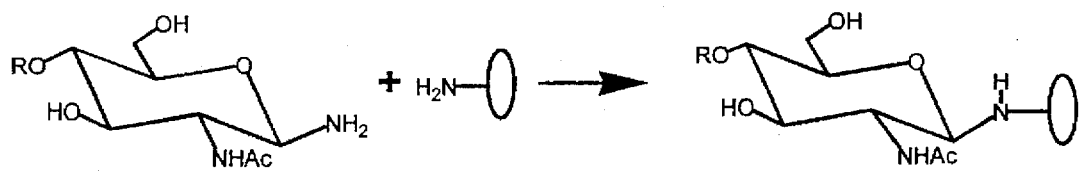
| SUGAR | REAGENT (−◯) |
|---|---|
| 14. R = H | 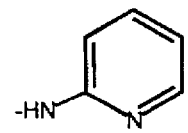 |
| 15 R = GlcNAc | 2-Hydrazinopyridine |
| 16. R = H | 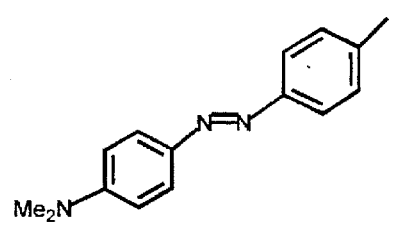 4-Amino-4'-dimethyl-aminoazobenzene |
Figure 3

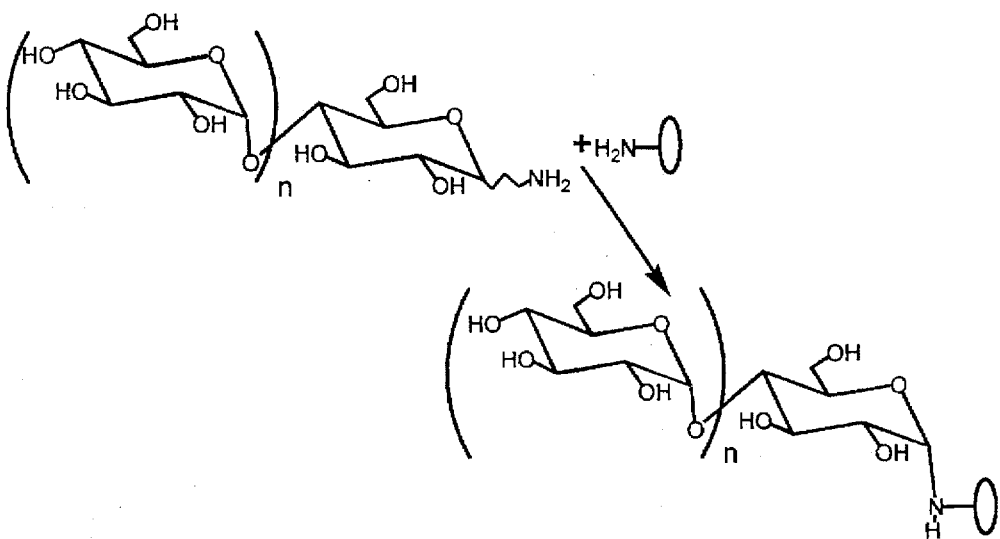

| SUGAR | REAGENT (-〇) |
|---|---|
| 17. n = 1  (1-Amino-1-deoxymaltobiose)<br>18. n = 2  (1-Amino-1-deoxymaltotriose)<br>19. n = 5  (1-Amino-1-deoxymaltohexaose)<br>20. n = 2-7 (mixture) | 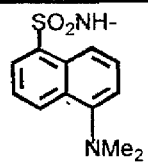<br>Dansyl hydrazine |
| 21. n = 1  (1-Amino-1-deoxymaltobiose)<br>22. n = 2  (1-Amino-1-deoxymaltotriose)<br>23. n = 5  (1-Amino-1-deoxymaltohexaose)<br>24. n = 2-7 (mixture) | 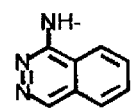<br>1-Hydrazinophthalazine |
| 25. n = 1  (1-Amino-1-deoxymaltobiose)<br>26. n = 2  (1-Amino-1-deoxymaltotriose)<br>27. n = 2-7 (mixture) | 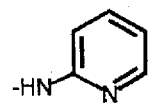<br>2-Hydrazinopyridine |

Figure 5

METHOD FOR PRODUCING SYNTHETIC N-LINKED GLYCOCONJUGATES

FIELD OF THE INVENTION

The present invention relates to synthetic N-linked glycoconjugates and, in particular, to a method for synthesizing N-linked glycoconjugates by reaction of glycosyl-1-amines with nucleophilic reagents.

BACKGROUND OF THE INVENTION

Carbohydrate moieties attached to proteins and lipids in naturally-occurring glycoproteins and glycolipids play prominent roles in a number of biological activities such as cell adhesion, microbial infection, fertilization, cancer metastasis and intracellular transport. It is therefore useful to study these carbohydrate moieties by preparing oligosaccharide derivatives by conjugation for example with chromophores, fluorophores or radioactive isotopes at the reducing end of the sugar.

Glycoconjugate probes derived by chemical modification of oligosaccharides are powerful tools not only for the structural analysis and elucidation of biological function, but may also be useful in the development of conjugate vaccines, clinical diagnostics and therapeutics. Applications for chromophoric and fluorescent glycoconjugates include carbohydrate analysis, for example by HPLC, capillary electrophoresis and resolution on polyacrylamide gels, and as substrates for studies employing glycosyl transferase and glycoprotein-processing enzymes. Neoglycolipids are useful in probing of TLC plates with purified receptors known to recognize oligosaccharides and as glycolipid analogs (GLAs) as immunomodulators. Chemiluminescent derivatives are useful in chemiluminescent-based immunoassays. Glycoconjugate probes are also useful as immobilized sugars in solid-phase systems, as derivatives of biotin for formation of stable multivalent complexes with avidin, as neoglycopeptides and neoglycoproteins, as specific binding molecules in diagnostic reagents and as polysaccharide-conjugate vaccines.

The numerous applications for glycoconjugate probes have inspired significant research in chemical reactions and coupling methods for the modification of oligosaccharides. There are a number of known methods for the synthesis of glycoconjugates (Lee, Y. C. et al *Glycoconjugates: Composition Structure and Function* H. J. Allen & E. C. Kisaulis, eds; Dekker, New York; 121;1992).

For example, reductive amination is a widely used technique for the preparation of a glycoconjugate wherein the reducing terminus of the oligosaccharide is reacted with an amino group of protein to form a Schiff adduct. The Schiff adduct is subsequently reduced with sodium cyanoborohydride to form a covalent bond between the aldehyde form of the sugar and a primary amine. Reductive amination has been used for the synthesis of neoglycoproteins (Gray, G. R. *Arch Biochem Biophys* 163:426;1974) and fluorescent conjugates (Hase, S. et al *J Biochem* 85:995; 1979).

However, reductive amination results in degradation of the reducing end monosaccharide due to ring-opening of the pyranose residue which may adversely affect the biological activity or immunogenicity of the carbohydrate moieties for in vivo studies (Kamicker, B. S. et al *Arch Biochem Biophys* 183:393;1977). The reaction time is very slow, typically many days, even when the sugar is present in large excess, which excess is uneconomical and requires a significant sample clean-up procedure. Moreover, the resultant secondary ammonium linkage and the acyclic ring of these conjugates may exert undesirable influence resulting in questionable use of this method to prepare immunogens containing oligosaccharide haptens where highly specific anti-carbohydrate antibodies are desired (Danielson, S. J. et al *Glycoconjugate J* 3:363;1986). It will be appreciated by those skilled in the art that it is important for biological studies that the integrity of the glycan residue suffers minimum perturbation during any modification that leads to the preparation of a glycoconjugate.

Another method for synthesis is by direct fluorescent labelling with 2-aminopyridine wherein the reducing sugar is fluorescently labelled by condensing directly with 2-aminopyridine under strong acidic conditions (Her, G. R. et al *J Carb Chem* 6:129;1987). However, the yield is low, the reaction is slow and requires acidic conditions, excess reagents and high temperatures. These conditions encourage the formation of by-products due to the degradation of carbohydrates by the browning reaction.

Risley, J. M. et al (WO88/04323, Jun. 16, 1988) describes a method for direct derivatization of the 1-amino function of glycosylamines. 1-Amino-1-deoxyoligosaccharide is prepared from a glycopeptide or a glycoprotein using a β-aspartylglycosylamineamidohydrolase. The resultant 1-amino-1-deoxyoligosaccharide is then reacted with a reactive acyl derivative, such as acid chloride or acid anhydride, at alkaline or neutral pH. The reaction occurs at the 1-amino functional group. However, acid chlorides are a very reactive species and there is a likelihood that O-acylation of the sugar hydroxyl groups will occur.

Manger, I. D. et al (Canadian Patent Application No. 2,023,339; published Feb. 17, 1991 and Canadian Patent Application Number 2,080,502; published Apr. 16, 1993) disclose a method wherein oligosaccharides are derivatized to form synthetic N-linked glycoconjugates by converting a glycosylamine derivative of the oligosaccharide to a haloacetylated derivative as an intermediate compound. Subsequent ammonolysis of the chloroacetamido function produces the corresponding 1-N-glycyl-β-derivative which is used to synthesize N-linked glycoconjugates. The haloacetylation reaction is carried out by reaction of the glycosylamine with an excess, typically 5- to 10-fold, of chloroacetic anhydride.

The above-mentioned methods preserve the pyranose form of the reducing end sugar of oligosaccharides, unlike the reductive amination method which degrades the reducing end sugar. However, both methods involve direct functionalization of the 1-amino function, a process which is inefficient and difficult to control because of the poor nucleophilicity of the 1-amino group and the tendency of glycosylamines towards dimerization and hydrolysis. A comparison of the basicity of the 1-amino ($pK_a$=5.2) and 2-amino ($pK_a$=7.7) functions is suggestive of the poor utility of the 1-amino function as a nucleophile. Even though small electrophiles, such as acetic anhydride and chloroacetic anhydride, react in a better fashion, the use of excess reagents is necessary, for example a 10-fold excess of the N-acetylation reagent, in the method of Manger et al.

The main drawbacks of the prior art methods described above are that they require the use of either excess reagents or a multi-step procedure. These are significant drawbacks when dealing with minute amounts of biologically important oligosaccharides from natural glycoconjugates.

In view of the many applications for glycoconjugate derivatives, it is an object of the present invention to provide a method for producing oligosaccharide derivatives which overcomes the disadvantages of the prior art.

SUMMARY OF THE INVENTION

According to the present invention, there is provided a method for the synthesis of an N-linked glycoconjugate comprising reacting a glycosyl-1-amine with a nucleophilic reagent, at conditions which favour nucleophilic substitution, by displacement of the 1-amino functional group.

BRIEF DESCRIPTION OF THE DRAWINGS

In drawings which illustrate embodiments of the present invention:

FIGS. 1, 2 and 3 are reaction schemes showing the preparation of synthetic N-linked glycoconjugates, conjugated with a number of chromophore and fluorophore labels, in accordance with the method of the present invention;

FIG. 5 is a reaction scheme showing the preparation of synthetic N-linked glycoconjugates conjugated with a number of chromophore and fluorophore labels, from 1-amino-1-deoxy-maltose and 1-amino-1-deoxy-maltooligosaccharides;

DETAILED DESCRIPTION OF THE PREFERRED EMBODIMENTS

Figure 1:
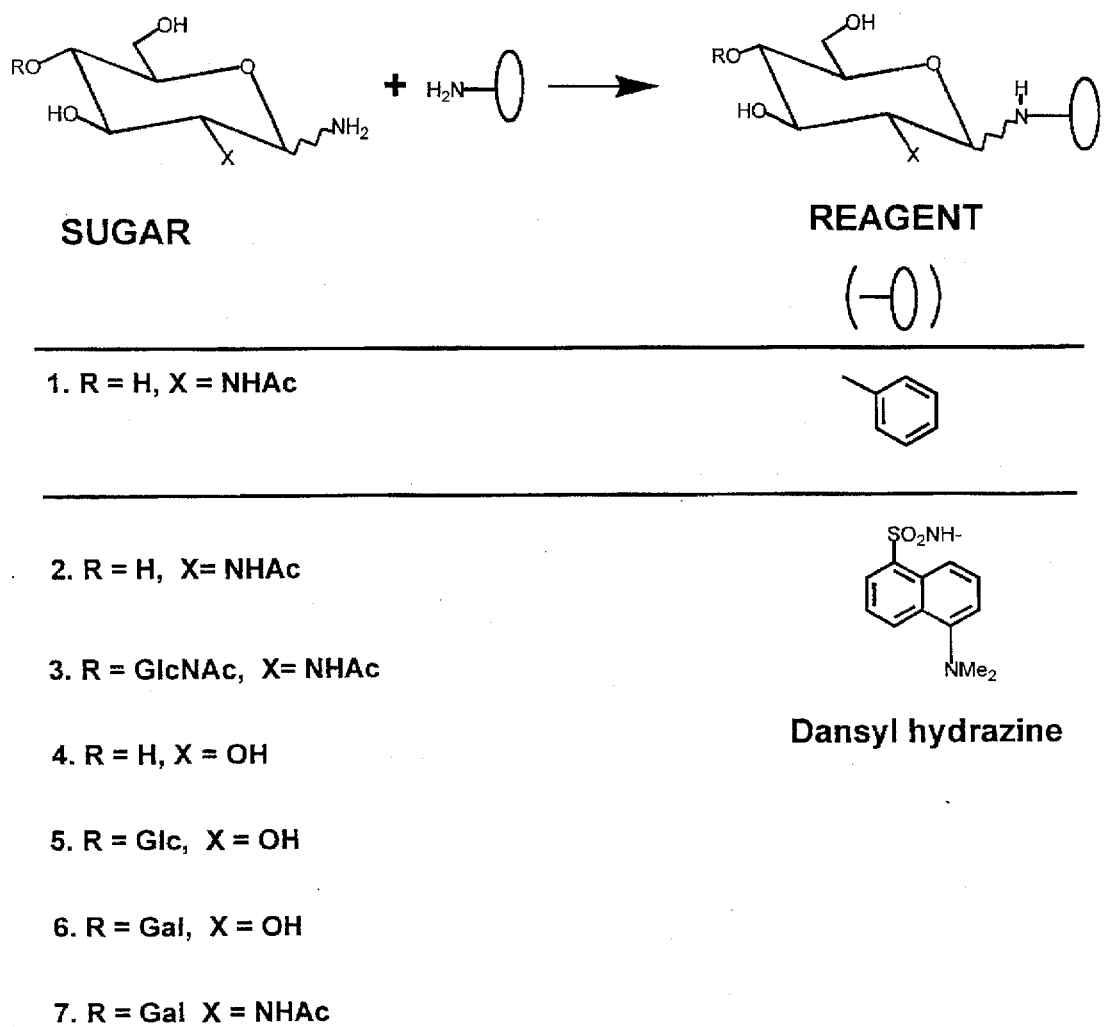

As mentioned previously herein, glycosyl-1-amines have a tendency to hydrolyse readily and to dimerize by self-condensation of two molecules by a "transamination" reaction via an acyclic immonium ion intermediate (Isbell, H. S. et al *J Org Chem* 23:1309;1958; Bolton, C. H. et al *Biochem J* 101:184;1966). Accordingly, the use of the 1-amino function as a nucleophile in the prior art techniques is an inefficient route for synthesis of glycoconjugates.

The present inventors have now discovered that they can exploit this instability of glycosyl-1-amines to prepare a broad spectrum of glycoconjugate probes useful in carbohydrate analysis, microsequencing, immunoassays and biorecognition studies. It was discovered by the present inventors that the dimerization process of unstable glycosyl-1-amines can be suppressed in the presence of a nucleophile which is more powerful than the glycosyl-1-amino group, under conditions which promote a nucleophilic substitution reaction.

In accordance with the present invention, glycosyl-1-amines are prepared by reaction with a nucleophile at the $C_1$ of the sugar by substitution of the 1-amino group. The 1-amino function itself is not modified as in the prior methods of Risley and Manger. The general reaction scheme is depicted below:

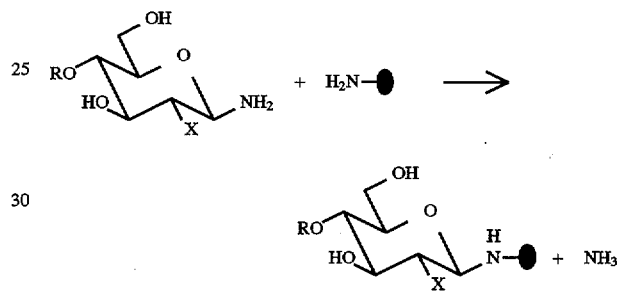

wherein X represents OH or NHAc.

The glycosyl-1-amines used in the present invention include any monosaccharide with a reducing end and any oligosaccharide having a reducing end monosaccharide. The oligosaccharide may be obtained from glycoproteins or glycolipids derived from microbial, plant or animal sources and those released by conventional enzymatic techniques, for example employing an endoglycosidase such as N-glycanase, Endo-F or Endo-H enzymes, or by chemical techniques known to those skilled in the art, for example by hydrazinolysis.

There are a number of methods known to those skilled in the art for the synthesis of glycosylamines. A one-step synthesis of amino sugar β-glycosylamines by direct condensation of free reducing monosaccharides with ammonium bicarbonate is described in Likhosherstov, L. M. et al (*Carbohydr Res* 146:C1;1986). The synthesis of β-glycosylamines via glycosyl azides involves several steps (Spinola, M. et al *J Biol Chem* 245:4158;1970; Cowley, D. E. et al *Carbohydr Res* 19:231;1971; Dunstan, D. et al *Carbohydr Res* 25:246;1970; Nakabayashi, S. et al *Carbohydr Res* 174:279;1988 and Paul, B. et al *Carbohydr Res* 80:99;1980). Isbell et al (*J Org Chem* 23:1309;1958) describes the reaction of a free reducing monosaccharide with ammonia and a primary amine. An enzymatic procedure for obtaining 1-amino-1-deoxyoligosaccharides from a glycopeptide or glycoprotein containing Asn-linked oligosaccharides is described in WO88/04323.

Suitable 1-amino-1-deoxy sugars are derived from glucose, mannose, fucose, galactose, cellobiose, lactose, N,N-diacetylchitobiose and N-acetyllactosamine.

Examples of nucleophilic reagents for use in the preparation of synthetic glycoconjugates according to the present invention are nucleophiles having a chromophore group, a fluorophore group, a chemiluminescent group, a lipid, an amino acid or peptide moiety, a linker/spacer group, a biotin group, or an affinity label. Preferably, the nucleophilic reagent has an —$NH_2$ or —$NHNH_2$ group.

Examples of nucleophilic reagents having a chromophore or a fluorophore group are substituted aliphatic and aromatic amines, hydrazines and benzylamines, such as dansyl hydrazine, 1-hydrazinophthalazine, 9-fluorenamine, isonicotinic hydrazide, 2-hydrazinopyridine and 4-amino-4'-dimethylaminoazobenzene.

Examples of chemiluminescent groups are luminol and analogs thereof, including N-(4-aminobutyl)-N-ethylisoluminol.

Suitable lipid nucleophiles are dipalmitoylphosphatidylethanolamine, dihexadecylglycerophosphoethanolamine, n-tetradecylamine, n-octylamine and cylcohexylamine.

Other nucleophilic reagents are peptides having lysine groups, such as L-lysllysine and Boc-Lys-OMe, and biotin hydrazide. The nucleophile reagent may also provide a linker/spacer group such as γ-aminobutyraldehydediethylacetal and 1-N-(9-fluorenomethoxycarbonyl)-6-diamino-hexane.

The nucleophilic reagent may also be isonicotinic hydrazide to form an isonicotinic hydrazide-saccharide conjugate.

In contrast to the prior art methods described previously herein, it is not necessary to provide a large excess of reagent to effect nucleophilic substitutions. In accordance with the present invention, the reaction proceeds at a good rate when the ratio of glycosylamine to nucleophilic reagent is in the range of from about 1:1 to about 1:2 by weight. A larger excess may be used but such an excess may be uneconomical and more dean-up is required.

The reaction is conducted at a temperature which favours nucleophilic substitution. For example, the reaction may be conducted at a temperature of about 50° C.

The reaction is carried out in the presence of an aprotic solvent such as pyridine, DMSO and DMF.

The average yields of the transamination reaction of the present invention are typically in the range of from about 65 to 75% based on the starling 1-amino sugar.

In accordance with the present invention, glycoconjugates are prepared in one step from the glycosyl-1-amine stage. This represents a distinct advantage over the technique of Manger et al wherein derivatives are prepared in three steps. Another advantage of the present invention is that the requirement for a substantial excess of reagents is obviated. Moreover, the reducing end sugar is not degraded during tagging with nucleophiles.

Analysis of the products of the transamination reaction of the present invention by $^1$H-NMR analysis indicate that the major product is the cyclic form of the sugar which tends to dominate the equilibrium. This is supported by the characteristic chemical shift and coupling constants (δ=4.3–4.7 ppm, J=8.0–9.0 Hz for β-H and δ=5.2 ppm, J=3.8 Hz for α-H) representing the anomeric protons, available only from the cyclic form.

A broad spectrum of glycoconjugate probes are synthesized using the transamination reaction of the present invention. The reaction allows attachment of chromophore and fluorophore groups for sensitive detection, purification and quantitation of mixtures of oligosaccharides for carbohydrate analysis using LC, HPLC, LC-MS and capillary electrophoresis. This has been successfully demonstrated with model saccharides of different sizes.

The attachment of lipid moieties produces neoglycolipids, potential applications for which include immunomodulators and probing of TLC plates with purified receptors known to bind oligosaccharides to evaluate individual N- and O-linked oligosaccharide species released from glycoproteins and proteoglycans as antigens and ligands for carbohydrate-binding proteins. Neoglycolipids produced by the reaction of the present invention are also useful as microsequencing tools because of the exceptional ionization properties in mass spectroscopy and because they can be detected with greater sensitivity than free oligosaccharides.

Glycoconjugates containing fluorophore groups have application in biorecognition applications for glycosyltransferase activity assays and for cell surface carbohydrate-binding macromolecule analysis by fluorescence microscopy, etc.

The synthetic N-linked glycoconjugates prepared in accordance with the present invention are readily detected by HPLC (reverse phase), capillary HPLC and mass spectroscopy (FAB and electrospray). Carbohydrate ligands labelled with chemiluminescent tags may find potential in applications such as diagnostic reagents. Chemiluminescent probes produced in accordance with the present invention are stable and can be produced in bulk to improve immunoassays and for other biochemical and histological applications wherein a biologically active specific activity label is required.

Other applications include the attachment of a linker/spacer for conjugation of a variety of groups, including proteins and solid supports, and the generation of glycoamino acids and glycopeptides.

The scope of the transamination reaction of the present invention is of such general utility that any carbohydrate that contains a reducing terminal sugar residue may be functionalized for the generation of a broad spectrum of glycoconjugate probes. This route offers a comprehensive and versatile strategy for the rapid, efficient and sensitive coupling, purification and characterization of oligosaccharides that are normally available in scarce mounts (usually derived from glycoproteins and other glycoconjugates from natural sources) using inexpensive reagents and easily accessible instrumentation and separation procedures. The method can be extended to other oligosaccharides which possess a reducing end monosaccharide residue. Using this technology, it is also possible to synthesize glycomimetics, compounds in which the glycosidic oxygen is replaced by a nitrogen atom, of biologically active carbohydrates such as inhibitors (e.g. antibiotics) with a view to synthesize glycoconjugates to improve the therapeutic profile or absorption.

The following Examples illustrate the present invention.

EXAMPLE 1

Functionalization of Oligosaccharides with Chromophore and Fluorophore Labels

The practicality of the transamination reaction of the present invention was demonstrated by reaction of 1-amino-2-acetamido-1,2-dideoxy-β-D-glucopyranose with a series of nucleophilic reagents carrying chromophore and fluorophore groups including dansyl hydrazine, 1-hydrazinophthalazine, 9-fluorenamine, isonicotinic hydrazide, and 2-hydrazinopyridine. The reaction mixture containing glycosylamine and a 1- to 2-fold excess by weight of the nucleophilic reagent were reacted overnight in pyridine at 50° C. The reaction was monitored by TLC ($CHCl_3$:MeOH, 1:1). The solvent was removed and the reaction mixture was passed over BIOBEADS SM-2™

(BioRad, Richmond, Calif.). Unreacted sugars, where necessary, were separated by passage through a column of BIOGEL-F2™ (BioRad, Richmond, Calif.), using absorbance at 254 nm as detection.

The products were characterized by TLC on silica gel, FAB or electrospray mass spectroscopy and $^1$H-NMR analysis. The transamination reaction was indicated by a downfield shift of resonance at δ=4.1 ppm (associated with the anomeric protons of the unsubstituted glycosyl-1-amine) to δ=4.3–4.7 ppm. The latter chemical shift is associated with the β-anomer of the synthetic glycoconjugate.

EXAMPLE 2

Glycoconjugates containing chromophore and fluorophore labels, were obtained from other 1-amino-1-deoxy-sugars derived from glucose, mannose, fucose, galactose, cellobiose, lactose, N,N-diacetylchitobiose and N-acetyllactosamine as tabulated in FIGS. 1, 2 and 3. The glycoconjugates were prepared as described in Example 1.

Figure 4:
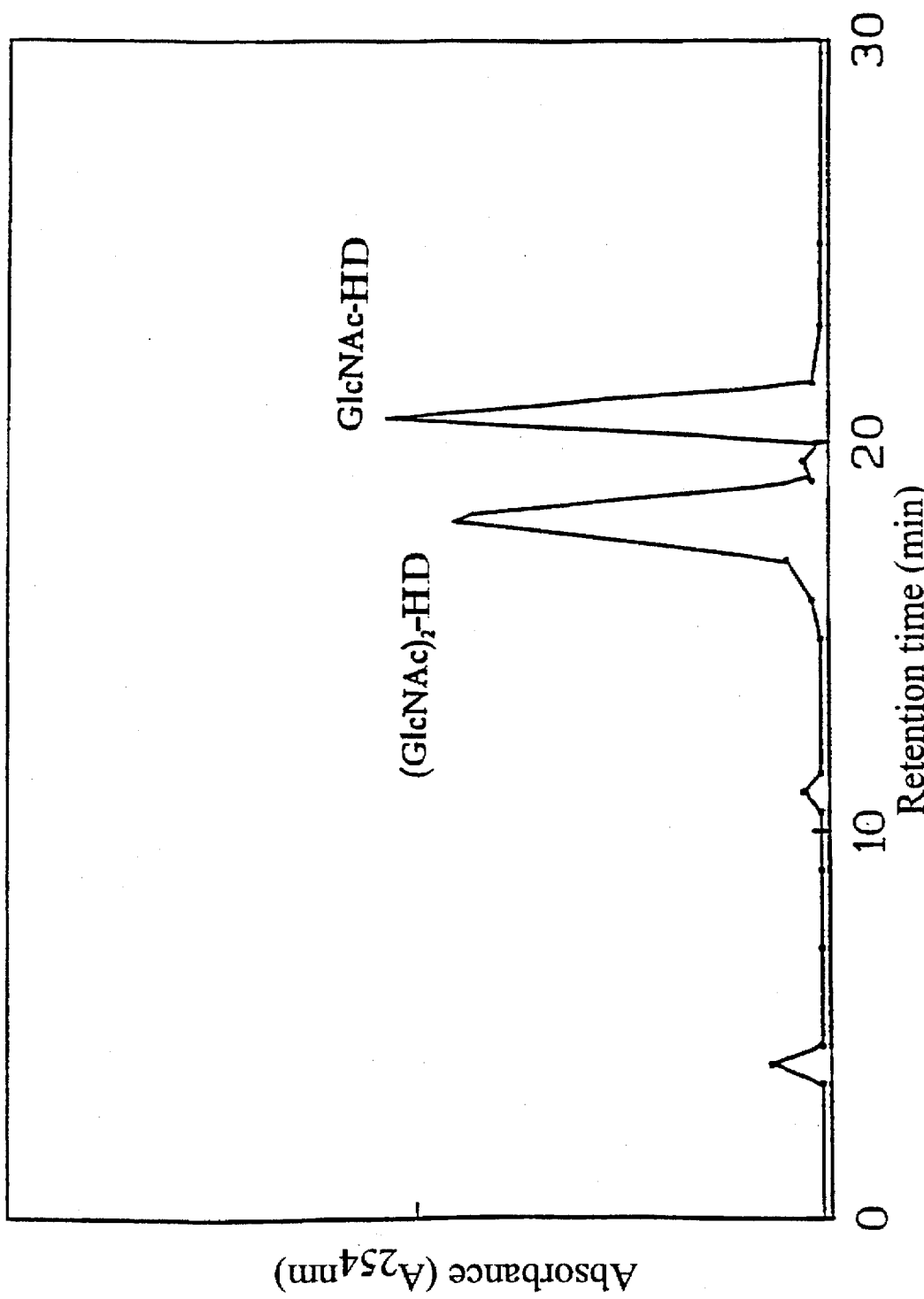
FIG. 4 is a chromatogram of a reverse phase HPLC elution profile of a mixture, containing synthetic N-linked glycoconjugate products obtained from the reaction of dansyl hydrazine (HD) with 1-amino derivatives of N-acetylglucosamine and N,N'-diacetylchitobiose (reaction products 2 and 3 of FIG. 1)

Purity of the glycoconjugates were verified on a SPHER-ISORB™ $C_{18}$ (5 μm) column (I.D. 300 μm) (Alltech, Deerfield, Ill.). A representative chromatogram depicting the separation of a mixture of reaction products 2 and 3 (FIG. 1) by reverse phase HPLC is shown in FIG. 4, in a 20% aqueous solution of $CH_3CN$ (isocratic mode).

EXAMPLE 3

The reaction is also applicable for the synthesis of oligosaccharide conjugates, as summarized in FIG. 5, illustrated by the reaction of 1-amino-1-deoxymaltooligosaccharides, having from 1–8 saccharide residues, with chromophore- and fluorophore-substituted hydrazines, including dansyl hydrazine, 1-hydrazinophthalazine, and 2-hydrazinopyridine. The reaction proceeded as described in Example 1.

Figure 6A:
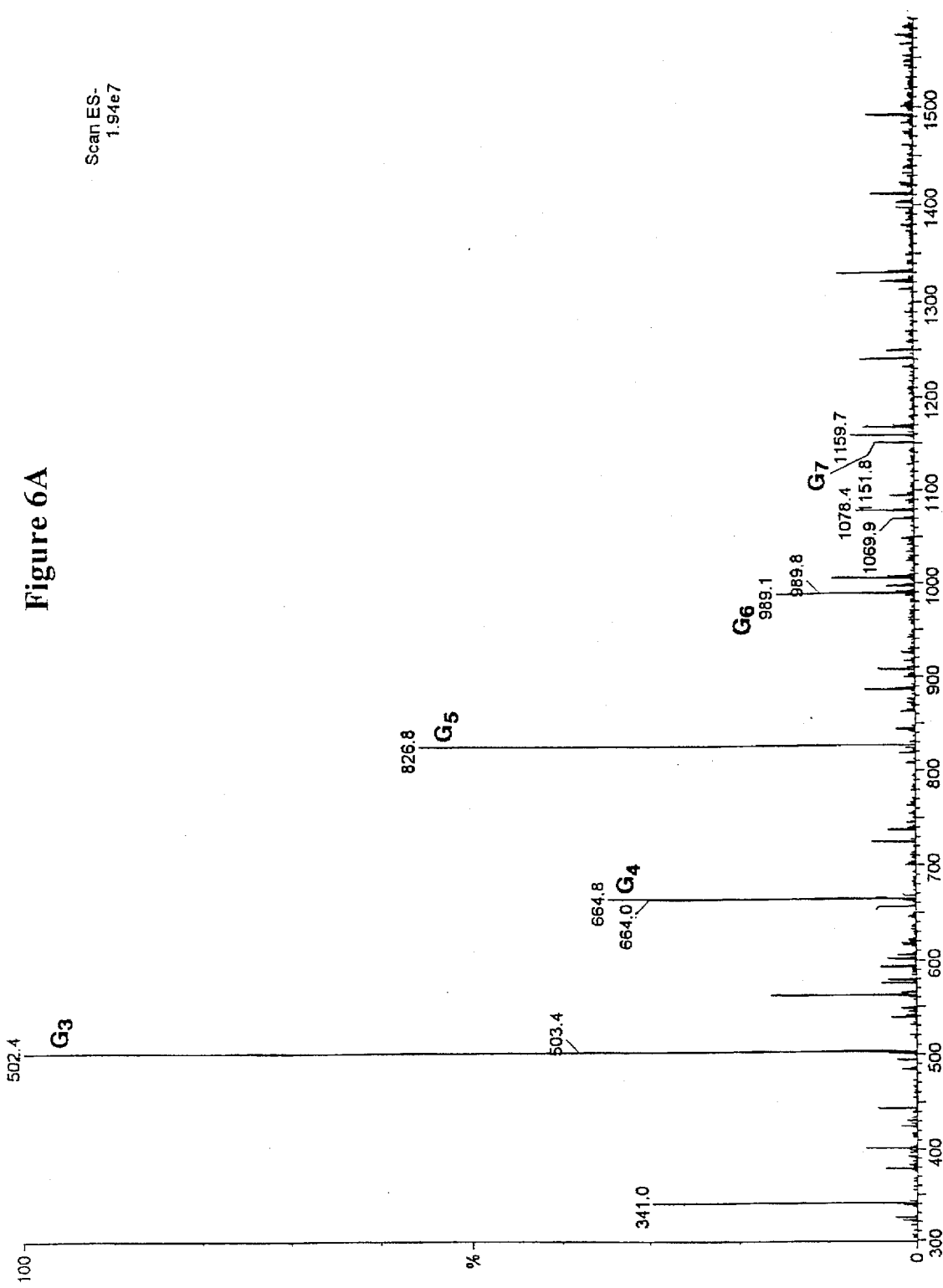
FIG. 6A is a reference negative ion electrospray mass spectrum of a starting material mixture of oligosaccharide-1-amines.
Figure 6B:
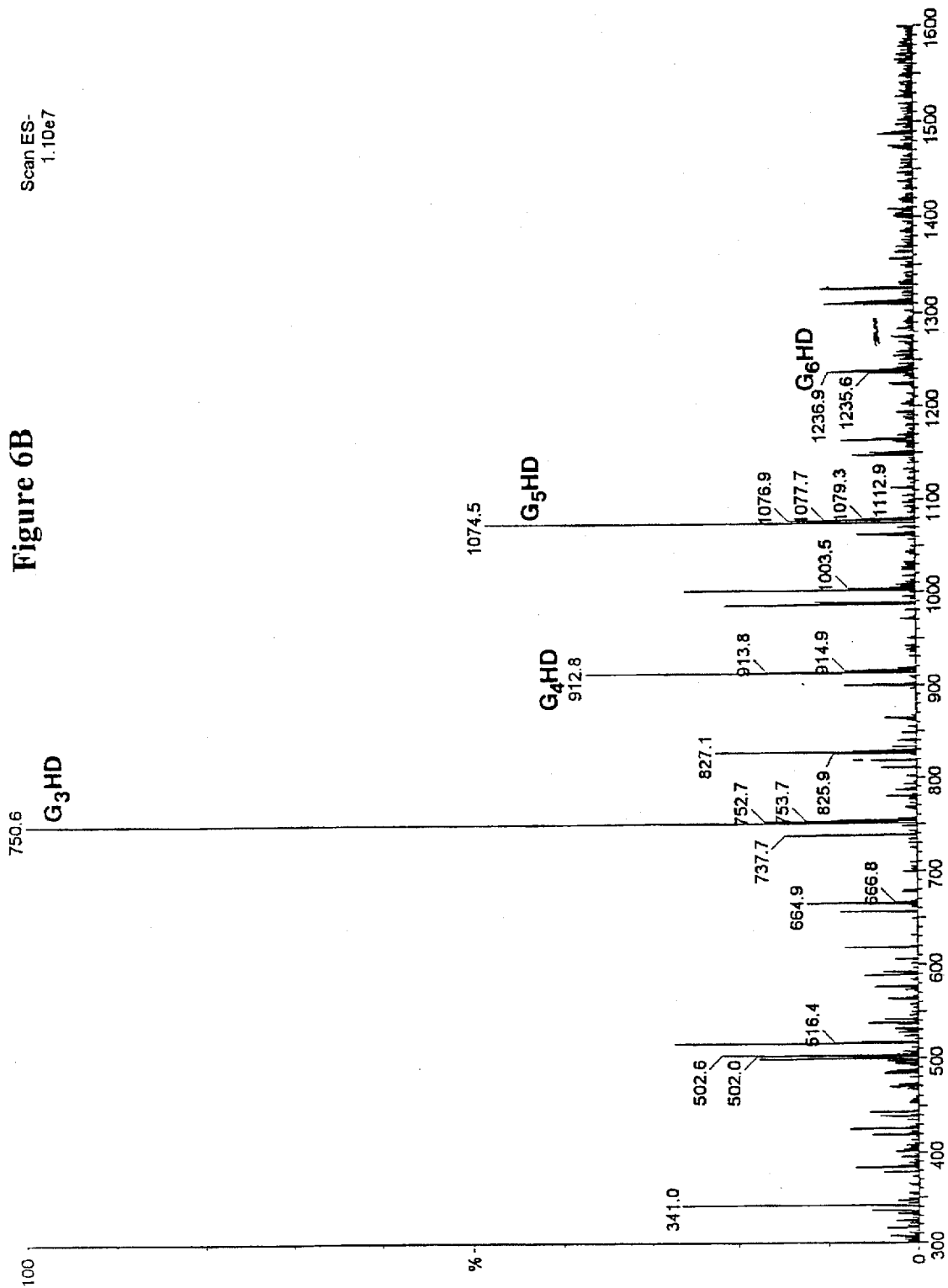
FIG. 6B is a negative ion electrospray mass spectrum confirming the preparation of synthetic N-linked glycoconjugates conjugated with N-dansyl hydrazino (HD), from the starting material of FIG. 6A, in accordance with the present invention.
Figure 6C:
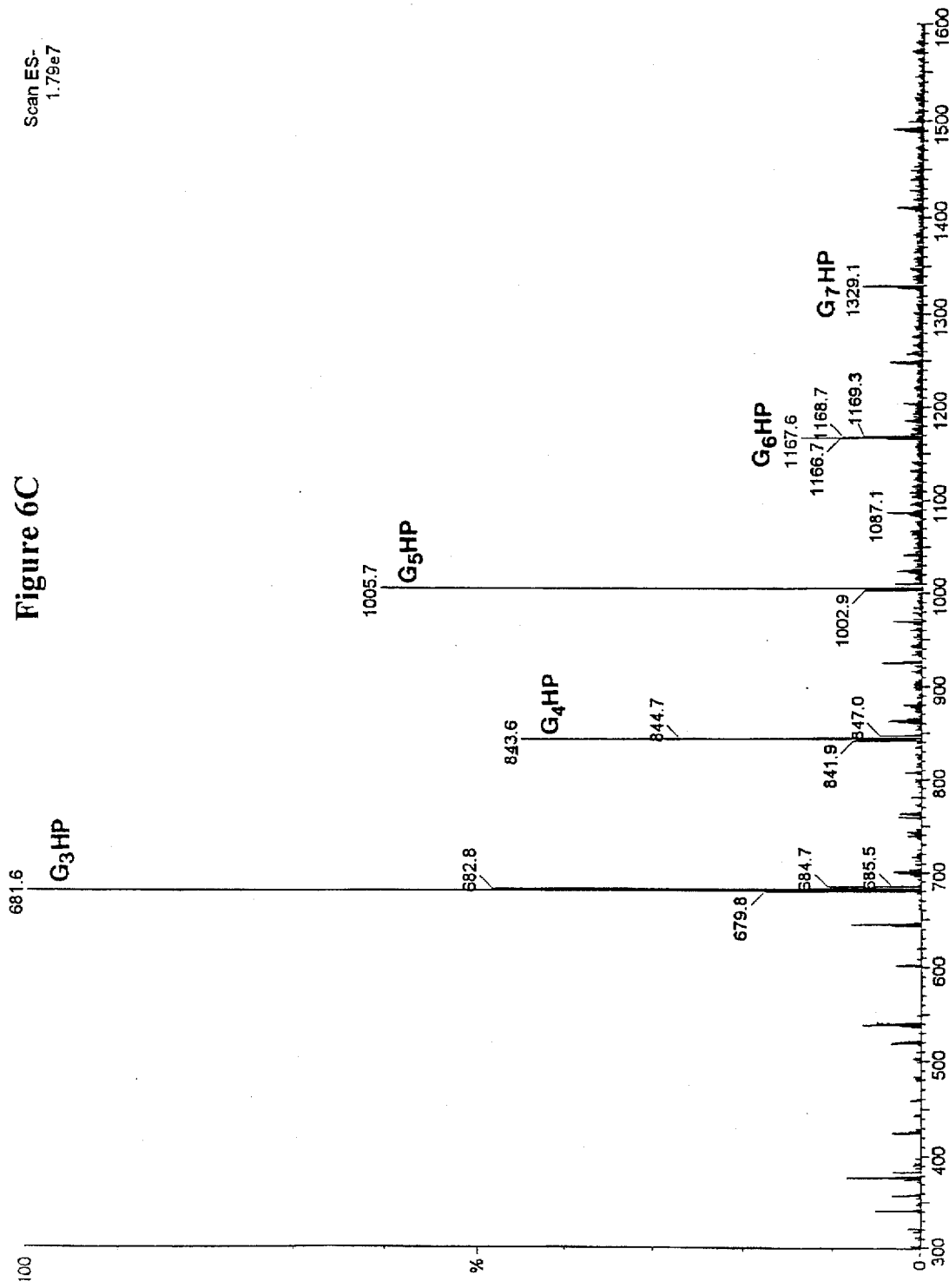
FIG. 6C is a negative ion electrospray mass spectrum confirming the preparation of synthetic N-phthalazine-substituted glycosylhydrazine (HP), observed as hydrochlorides, from the starting material of FIG. 6A, in accordance with the present invention.

The preparation of synthetic N-linked glycoconjugates was confirmed by electrospray mass spectroscopy. FIGS. 6A, 6B and 6C are negative ion electrospray mass spectra obtained by the products of the reaction of a standard mixture of 1-amino-1-deoxy-maltooligosaccharides, comprised of $G_3$=28%, $G_4$=16%, $G_5$=38%, $G_6$=14%, $G_7$=1%, $G_8$=0.5%; wherein $G_n$ represents the number of glucose residues, with dansyl hydrazine (HD) and 1-hydrazinophthalazine hydrochloride (HP), respectively. FIG. 6A shows the molecular mass of the starting material (1-aminomaltooligosaccharide) and FIG. 6B shows the molecular mass of the 1-aminooligosaccharide after derivation with dansyl labels. Similarly, FIG. 6C shows the molecular mass of the 1-aminomaltooligosaccharide, after derivation with hydralazines (observed as hydrochlorides). The successful attachment of chromophore and fluorophore labels provides an effective strategy for the sensitive detection and separation in liquid chromatography based systems.

In the case of maltooligosaccharides, wherein individual residues are connected by Glc-α-1→4-Glc linkages, the glycoconjugate products were characterized to have an α-gylcosylamine configuration exclusively.

Figure 7:
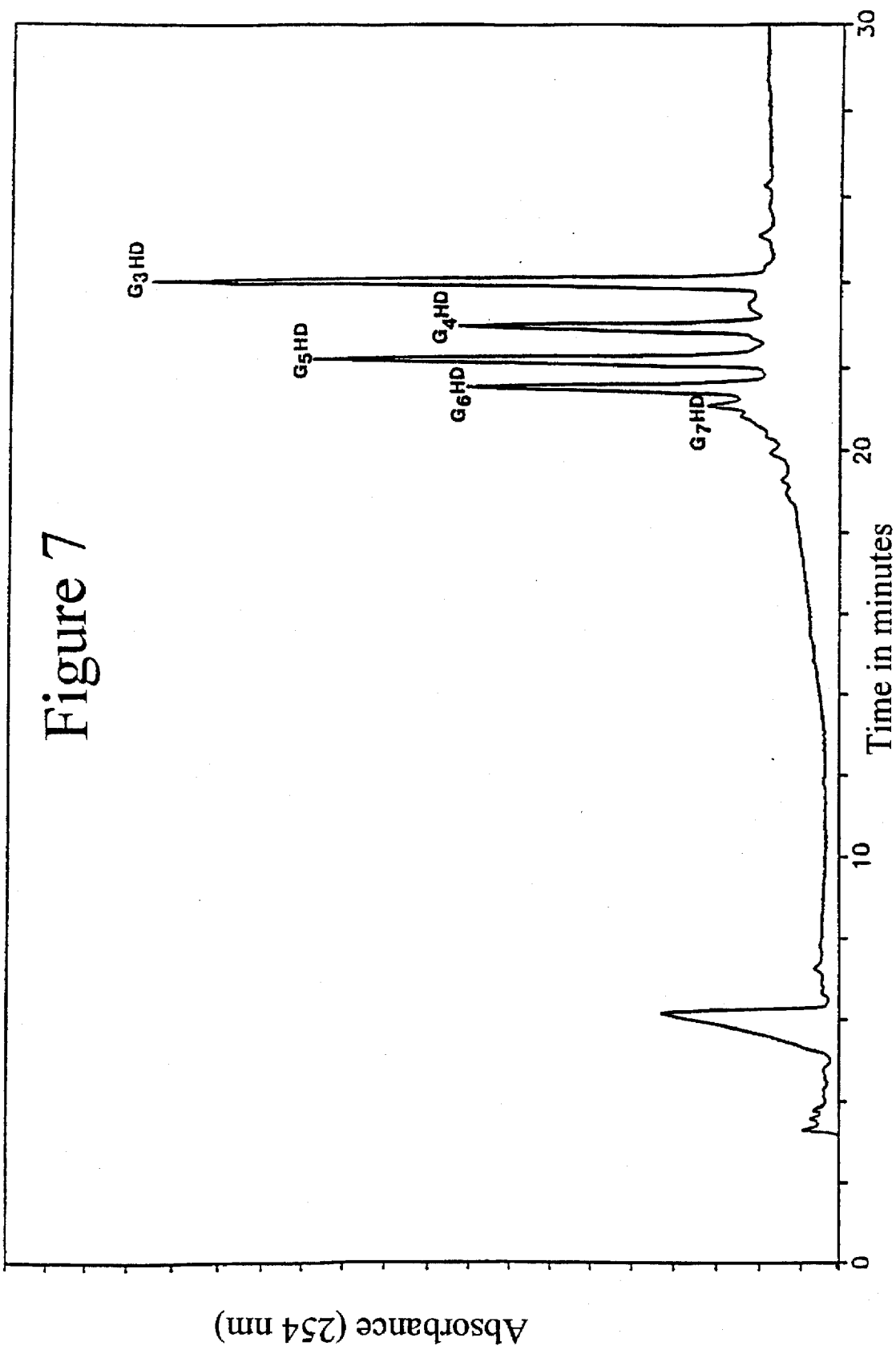
FIG. 7 is a graphical representation showing the reverse phase capillary HPLC ($C_{18}$) elution profile of product (20) resulting from the reaction of glycosyl-1-amine derivatives of a mixture of $G_3$–$G_7$ maltooligosaccharides with dansyl hydrazine.
Figure 8A:
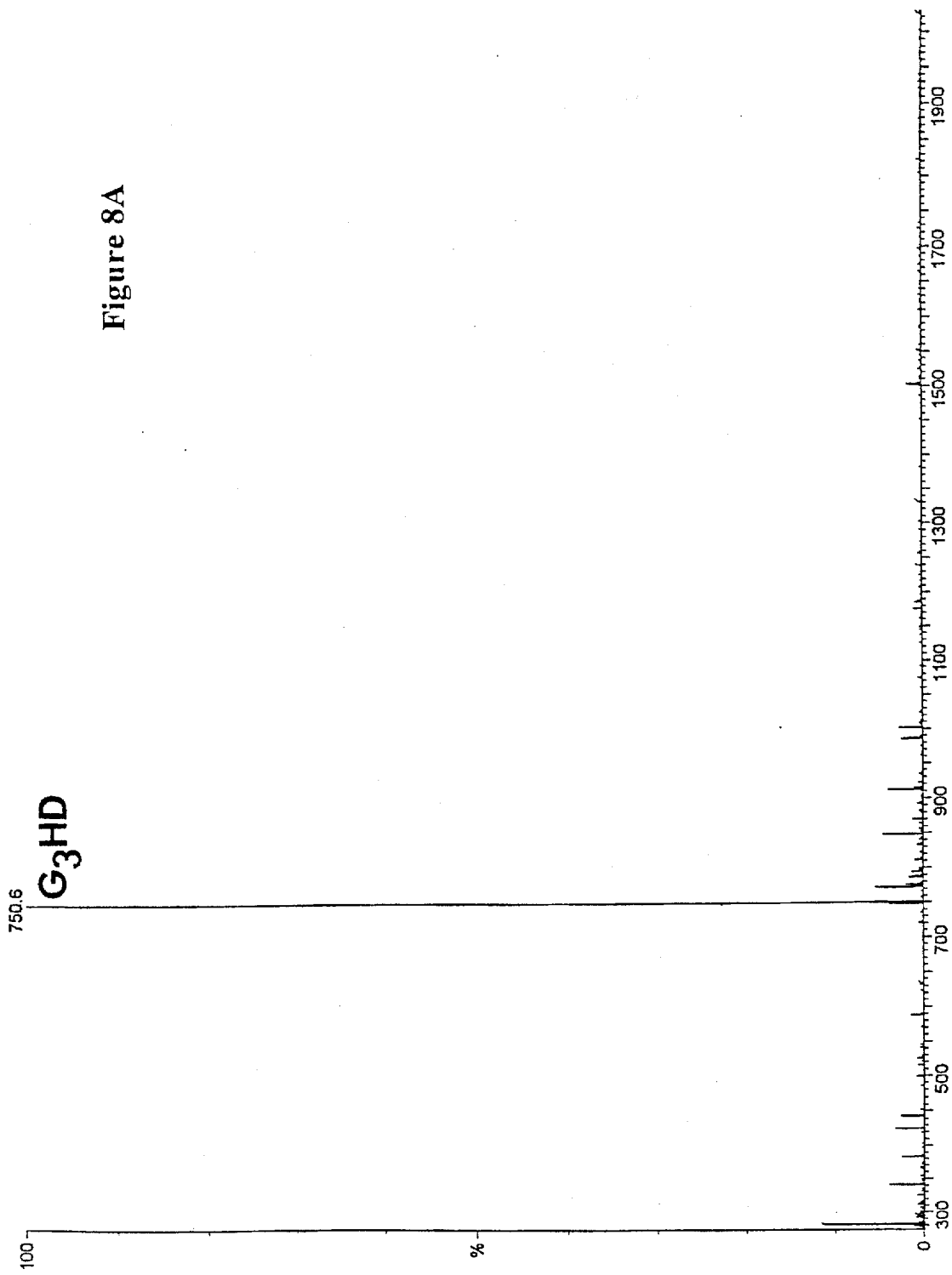
FIGS. 8A, 8B, 8C and 8D show negative ion electrospray mass spectra of the purified fractions of the BIOGEL P-2™ chromatography of N-dansylhydrazine coupled oligosaccharide conjugates, derived from a reaction mixture of dansyl hydrazine (HD) with 1-amino-1-deoxy-maltooligosaccharides for trisaccharide, tetrasaccharide, pentasaccharide and hexasaccharide, respectively.
Figure 8B:
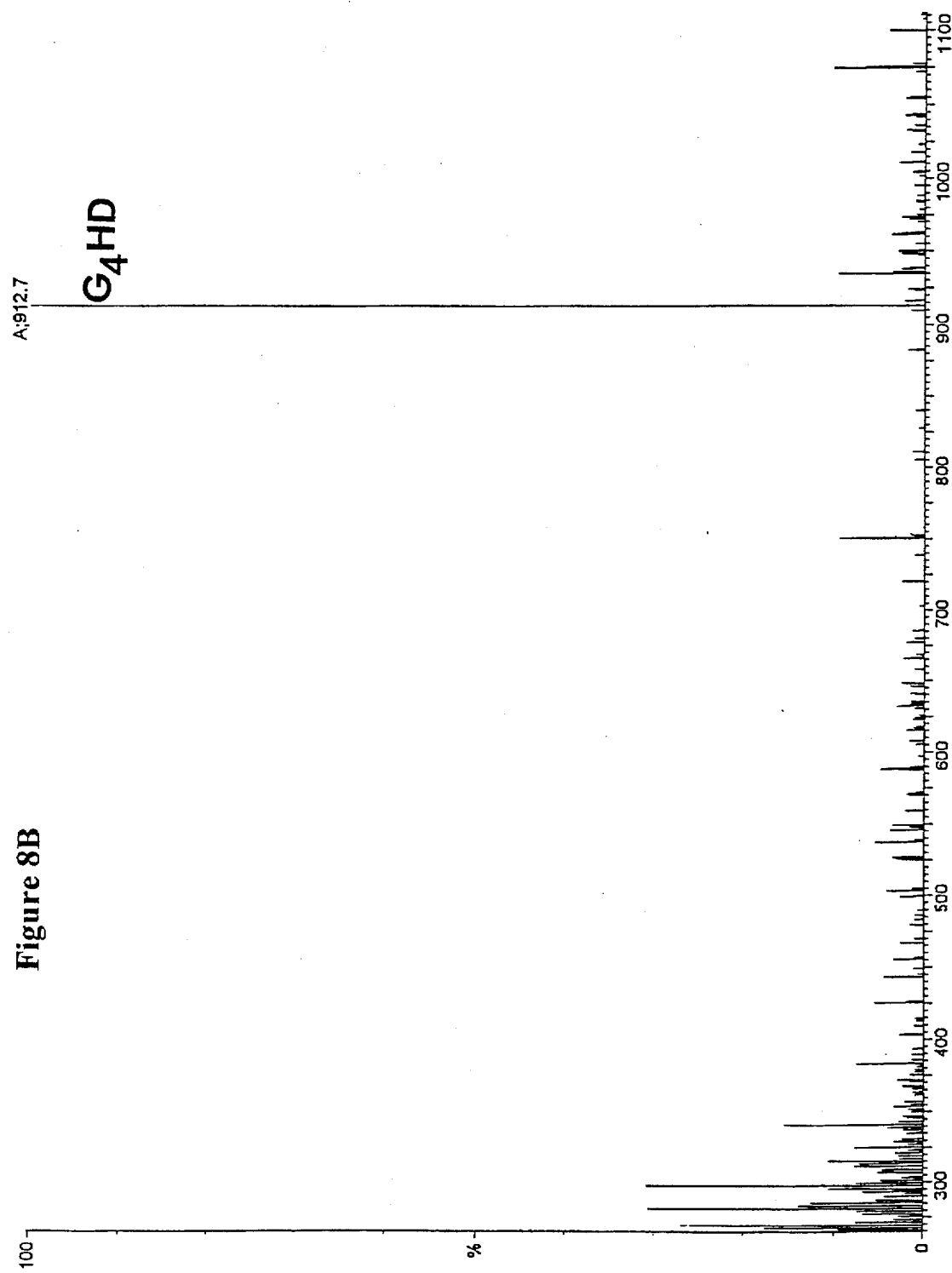
Figure 8C:
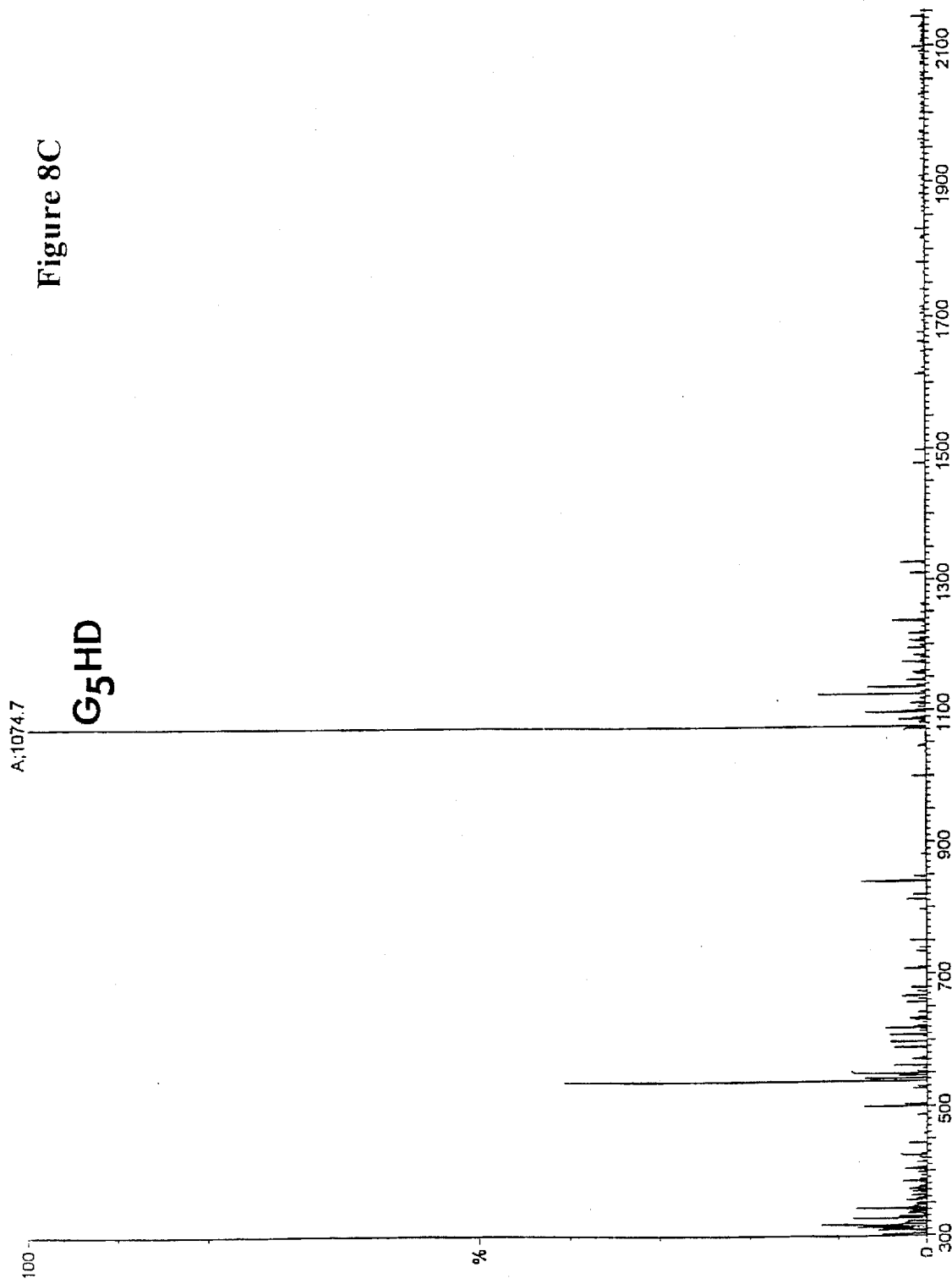
Figure 8D:
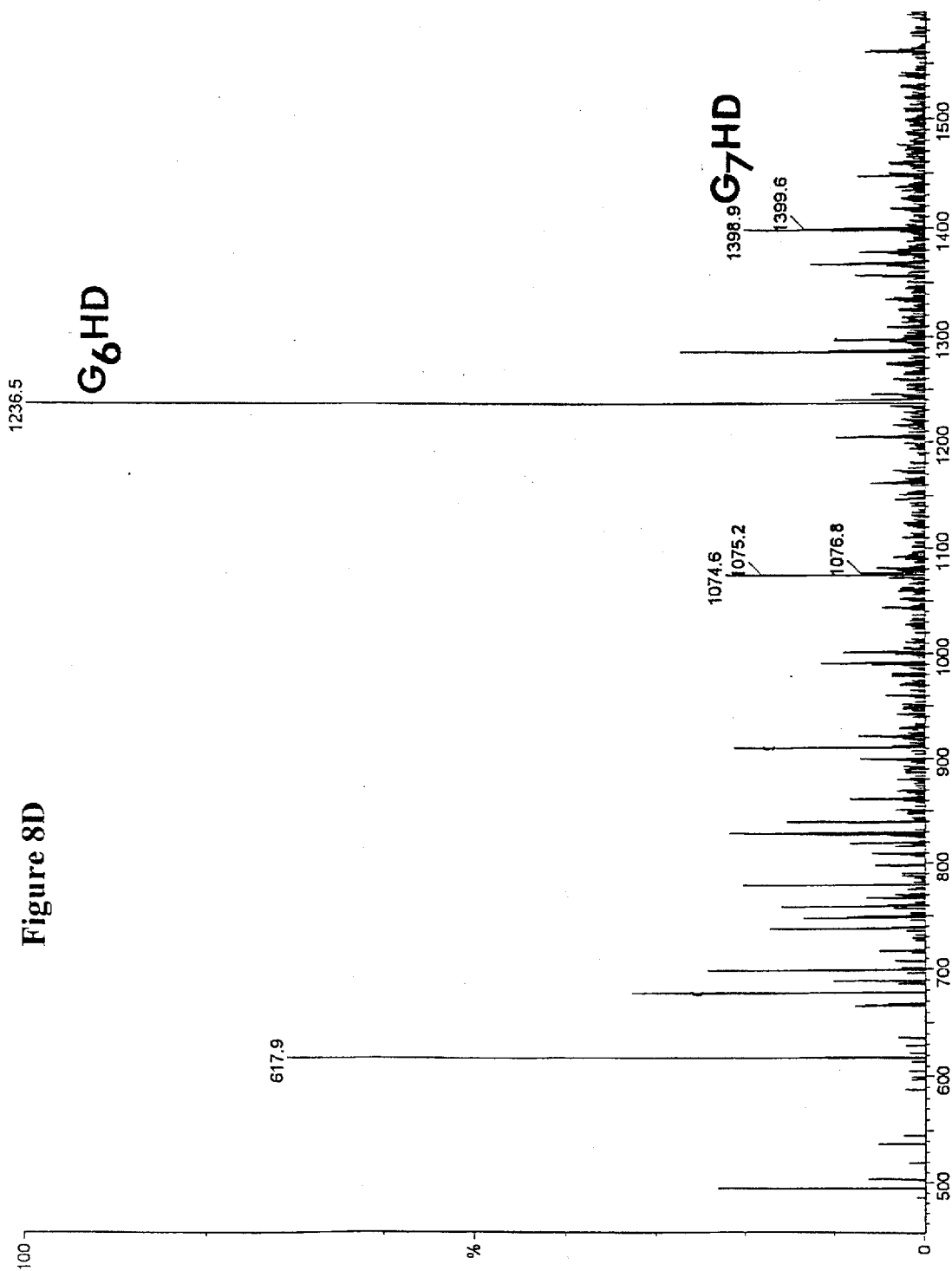

A representative chromatogram depicting the separation of a mixture of dansyl hydrazine substituted 1-amino-1-deoxy-maltooligosaccharides ($G_3$–$G_7$), on a capillary HPLC ($C_{18}$) column is shown in FIG. 7, using a gradient of acetonitrile and water.

As a consequence of this strategy, oligosaccharides having up to eight saccharide units were functionalized with chromophore and fluorophore tags, which were detected by capillary HPLC ($C_{18}$). This is supported by the individual electrospray mass spectra of the BIOGEL P-2™ purified 1-N-dansyl hydrazine substituted-1-deoxy-maltooligosaccharides (FIGS. 8A, 8B, 8C and 8D). Detection of about 100 pmol of the conjugated oligosaccharide was possible in the capillary HPLC system using an absorbance detector at 254 nm. The sensitivity level could be enhanced several-fold by employing fluorescence monitoring which extends the detection limits compared to UV monitoring.

The dansyl hydrazine substituted saccharides were also detected by capillary electrophoresis as borate complexes, whereby femtomolar amounts of sugars were detected and separated. Therefore, the conjugated oligosaccharides may also serve as substrates in glycosyl transferase assay studies, where the availability of sugar products is limited (Zhao, J. Y. et al *Glycobiology* 4:239;1994). Furthermore, these hydrophobic tails promote surface activity of the matrix during mass spectroscopy measurements. The presence of a secondary amine functional group serves as a site for protonation inducing characteristic fragmentation patterns useful for extracting valuable information about molecular weight and oligosaccharide sequence (Webb, J. W. et al *Anal Biochem* 169:337;1988; John, C. M. et al *Anal Biochem* 187:281;1990).

The data of Examples 1, 2 and 3 extensively support the usefulness of the present invention as an effective strategy for the functionalization of oligosaccharides with a variety of chromophore and fluorophore labels and their subsequent sensitive detection, purification and characterization, using liquid chromatography systems, including HPLC, capillary HPLC and capillary electrophoresis. Furthermore, the fact that the chromophore and fluorophore conjugated oligosaccharides could be detected both by capillary HPLC and mass spectroscopy (FAB and electrospray) indicates that an LC-MS (Liquid Chromatography—Mass Spectroscopy) detection strategy could be built upon the results obtained from such studies. In addition, this reaction provides a general route for the attachment of fluorescent probes to saccharides, which serve as effective tools to detect endogenous sugar receptors in histopathology (Gabius, H. J. et al *Lectins and Glycoconjugates in Oncology* Springer-Verlag, N.Y., 1988). In accordance with the present invention, an appropriate selection of chromophore and fluorophore labels can be made for the generation of synthetic N-linked glycoconjugates from an array of reagents which have been shown to react readily with glycosyl-1-amines, in high yields.

EXAMPLE 4

Functionalization of Oligosaccharides with Chemiluminescent Labels

In view of the demonstrated significance of complex carbohydrates in receptor-mediated events such as microbial infection (Karlsson, K. A. *Ann Rev Biochem* 58:309;1989) and mammalian cell-cell adhesion (Feizi, T. *Curr Opinion in Structural Biol* 3:701;1993), biochemical assays pertaining to carbohydrate-binding proteins deserve special attention. Chemiluminescent-based assays offer several advantages over other conventional protein-binding assays, for example, assays based on radiolabels (Campbell, A. K. et al *Methods Biochem Anal* D. Glick ed; 31:317;1985). Radioactive labels are unstable, hazardous, pose waste disposal problems and may require long times for incubation and counting.

In view of its sensitivity, chemiluminescence has left a remarkable impact on biochemical and biomedical analyses (Van Dyke, K. *Bioluminescence and Chemiluminescence: Instruments and Applications* CRC Press, 1985). Chemiluminescent-based assays take only a few minutes, are amendable to automation, and fall in the femtomole to attomole range, unlike spectrophotometric (sensitivity in the micromolar to nanomole range) and fluorometric assays (sensitivity in the nanomole to picomole range). Luminol and its structural analogs, for example N-(4-aminobutyl)-N-ethylisoluminol (ABEI) are the most widely studied chemiluminescent labels (Avigliano, L. et al *Anal Biochem* 159:67;1986; Roswell, D. F. et al *Methods Enzymol.* 57:409;1978). They are useful as labelling reagents for sensitive detection in HPLC (Kawasaki, T. et al *J Chrom* 328:121;1985; Imai, K. *Methods Enzymol* 133:435;1986) and in chemiluminescence-based immunoassays. However, the prior art methods of conjugation of chemiluminescent labels to carbohydrate moieties adversely affect the integrity of the reducing end saccharide residue.

The synthesis of glycoconjugates, containing a chemiluminescent label is demonstrated by the reaction of 1-amino-2-acetamido-1,2-dideoxy-β-D-glucopyranose with N-(4-aminobutyl)-N-ethylisoluminol (reaction 28, FIG. 9), in accordance with the present invention. The reaction was conducted as described in Example 1.

The method can be extended to other oligosaccharides which possess a reducing end monosaccharide residue. As a consequence, carbohydrate ligands labelled with chemiluminescent tags may find potential in applications such as diagnostic reagents.

EXAMPLE 5

Synthesis of Neoglycolipids

The synthetic attachment of glycan moieties to lipid residues has been shown to produce dramatic alterations in their physical and biological properties. Synthetic glycosylamides, with long alkylamine and fatty acid residues were shown to exhibit remarkable immunostimulant activity (Lockhoff, O. *Angew Chem Int Ed Engl* 30:1611;1991). N-alkyl-N-glycosyl fatty acid amides have been shown to enhance the production of antibodies in immunological test systems. Their unique mode of action was shown to differ from known adjuvants, presenting themselves as valuable candidates for immunization of patients with T-lymphocyte dysfunction, for example AIDS patients. One of the effective strategies in the development of vaccines is immunomodulation and since glycosylamides were shown to possess this remarkable property, synthesis of neoglycolipids, intermediates for the synthesis of the former, is of particular interest.

Neoglycolipids have been shown to be useful to probe TLC plates with purified receptors known to recognize oligosaccharides, to coat and to form liposomes designed for targeted drug delivery (Tang, P. W. et al *Biochem Biophys Res Commun* 132:474;1985; Childs, R. A. et al *Biochem* 262:131;1989). Thus, oligosaccharides derived from natural sources have been coupled to lipids such as dipalmitoylphosphatidylethanolamine to probe the roles of saccharides as recognition markers in biological systems (Feizi, T. et al *Methods Enzymol* 230:484;1994; Bezouska, K. et al *Nature* 373:150;1994; Pohlentz, G. et al *Eur J Biochem* 203:387;1992). However, as indicated earlier, this technique utilizes the reductive amination procedure which adversely affects the integrity of the reducing saccharide residue. Hence, there is a need for a method which maintains the integrity of the reducing end sugar residue.

Figure 9:
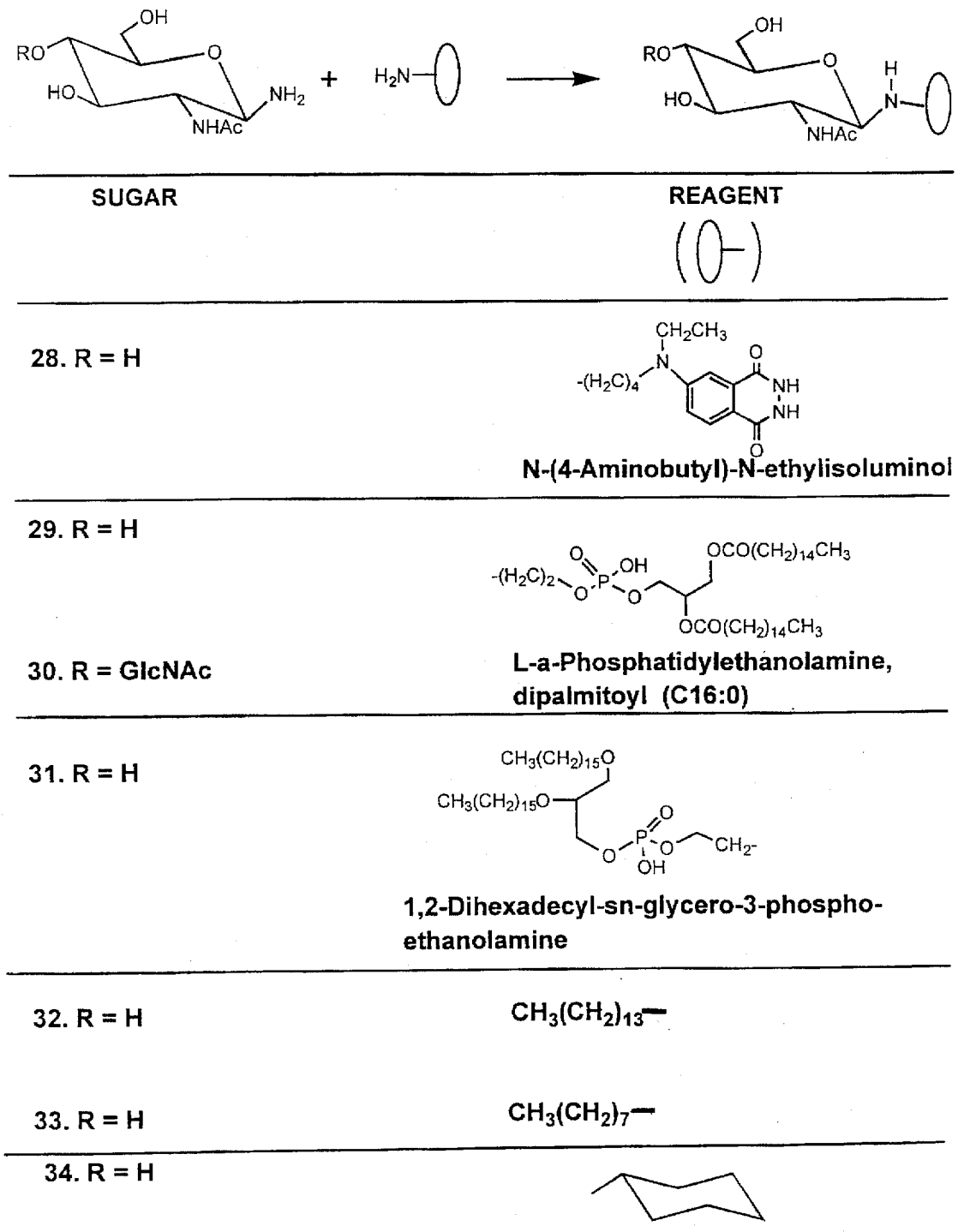
FIG. 9 is a reaction scheme showing the preparation of synthetic N-linked glycoconjugates conjugated with a chemiluminescent label and glycolipids, in accordance with the present invention.

Glycoconjugates were prepared according to reactions 29-34 of FIG. 9 according to the reaction of Example 1 to illustrate the successful accomplishment of maintaining the intactness of the pyranose ring at the reducing end. Neoglycolipids were formed by the reaction of 1-amino-1-deoxy-N,N-diacetylchitobiose with L-1,2-dipalmitoyl-sn-glycero-3-phosphoethanolamine and by the reaction of 1-amino-2-acetamide-1,2-dideoxy-β-D-glucopyranose with n-tetradecylamine and n-octylamine afforded their respective glycolipid derivatives (32 and 33). The latter is an aza-analog of octyl-β-D-glucopyranoside, which is an O-glycoside and a popular detergent in the studies involving membrane proteins. They are also valuable intermediate for the synthesis of glycosylamides, useful as potential immunomodulators.

A neoglycolipid was also formed by reaction of cyclohexylamine with the 1-amino derivative of N-acetylglucosamine afforded the cyclohexyl group substituted β-glycosylamine product (34). Such compounds are useful models for the generation of glycosteroids. Glycosteroids are gaining recognition as membrane permeation enhancers used for drug transport, e.g. for oral delivery of drugs whose bioavailability is restricted by their inability to penetrate intestinal epithelia.

Figure 10:
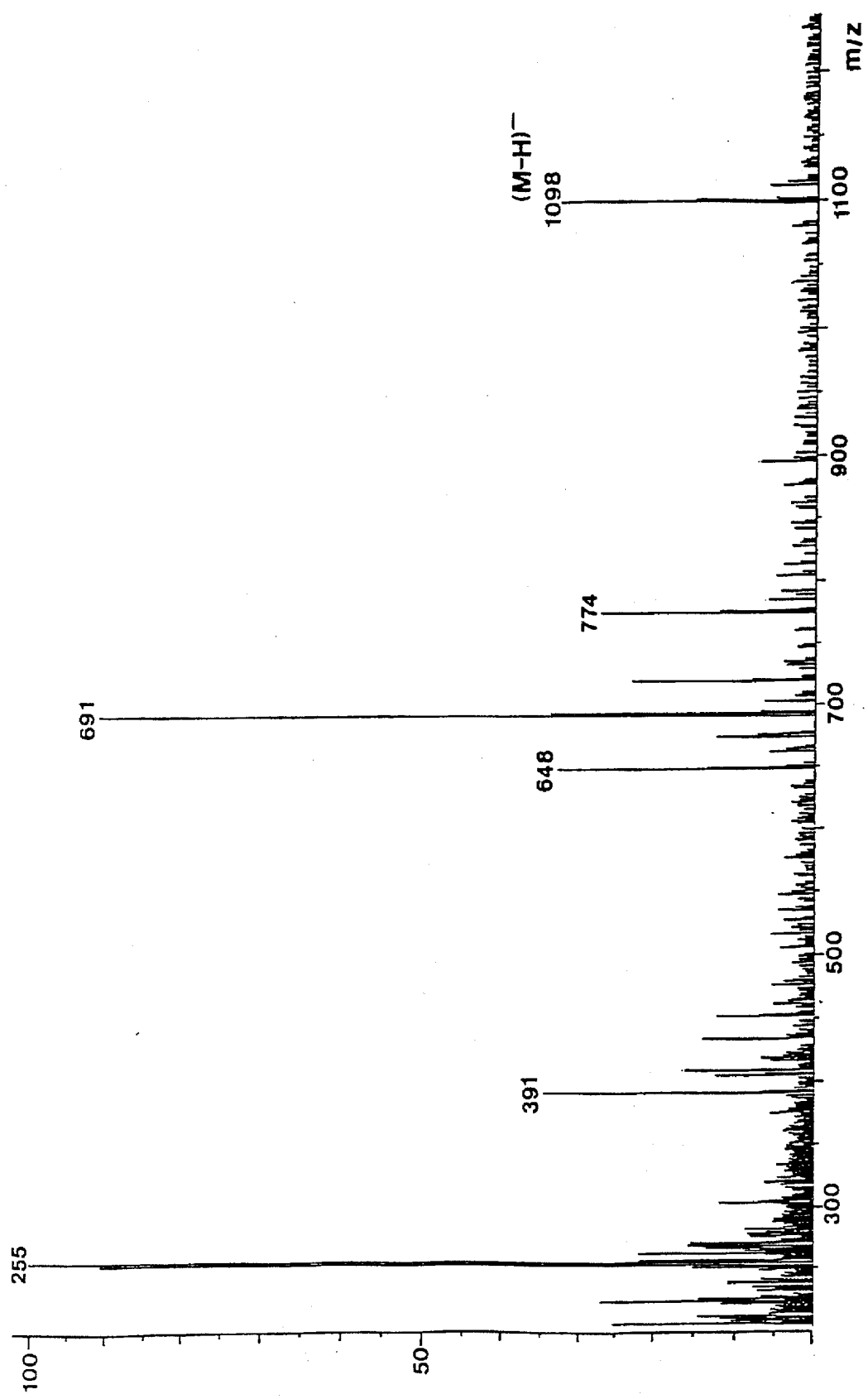
FIG. 10 is a negative ion FAB mass spectrum confirming the preparation of a neoglycolipid (30), in accordance with the present invention.

FIG. 10 is a negative FAB mass spectrum of the neoglycolipid (30) which displays the molecular mass of the product formed by the reaction of 1-amino-1-deoxy-N,N-diacetylchitobiose with L-1,2-dipalmitoyl-sn-glycero-3-phosphoethanolamine.

EXAMPLE 6

Synthesis of Neoglycopeptides

Neoglycopeptides may be formed by the conjugation of carbohydrates to peptides, either via a peptide bond or via an amine linkage formed by reductive amination or Amadori rearrangement (Meldal, M. *Curr Opinion Structural Biol* 4:710;1994; Lee, Y. C. et al *Glycoconjugates: Composition Structure and Function* H. J. Allen & E. C. Kisaulis, eds; Dekker, New York; 121;1992). Glycosylamines have been attached to the side chains of aspartic acid or glutamic acid derivatives (Christiansen-Brains et al *J Chem Soc Perkin Trans* I:1461;1993) and the resulting building blocks have been used for the synthesis of modified peptides with biological activity. L-lysyllysine has been employed, as a suitable backbone, to construct multivalent ligands of carbohydrate antigens (Ponpipom, M. M. et al *J Med Chem* 24:1388;1981; Fendersen, B. A. et al *J Exp Med* 160:1591;1984) for the development of synthetic vaccines against tumors (Toyokuni, T. et al *Tetrahedron Lett* 31:2673;1990). Conjugation of polysaccharides (which are often T-cell independent) to protein carriers has been used to convert them into T-cell dependent antigens with enhanced immunogenicity, which have the potential to be vaccine candidates (Jennings, H. J. *Adv Carb Chem Biochem* 41:155;1983).

Figure 11:
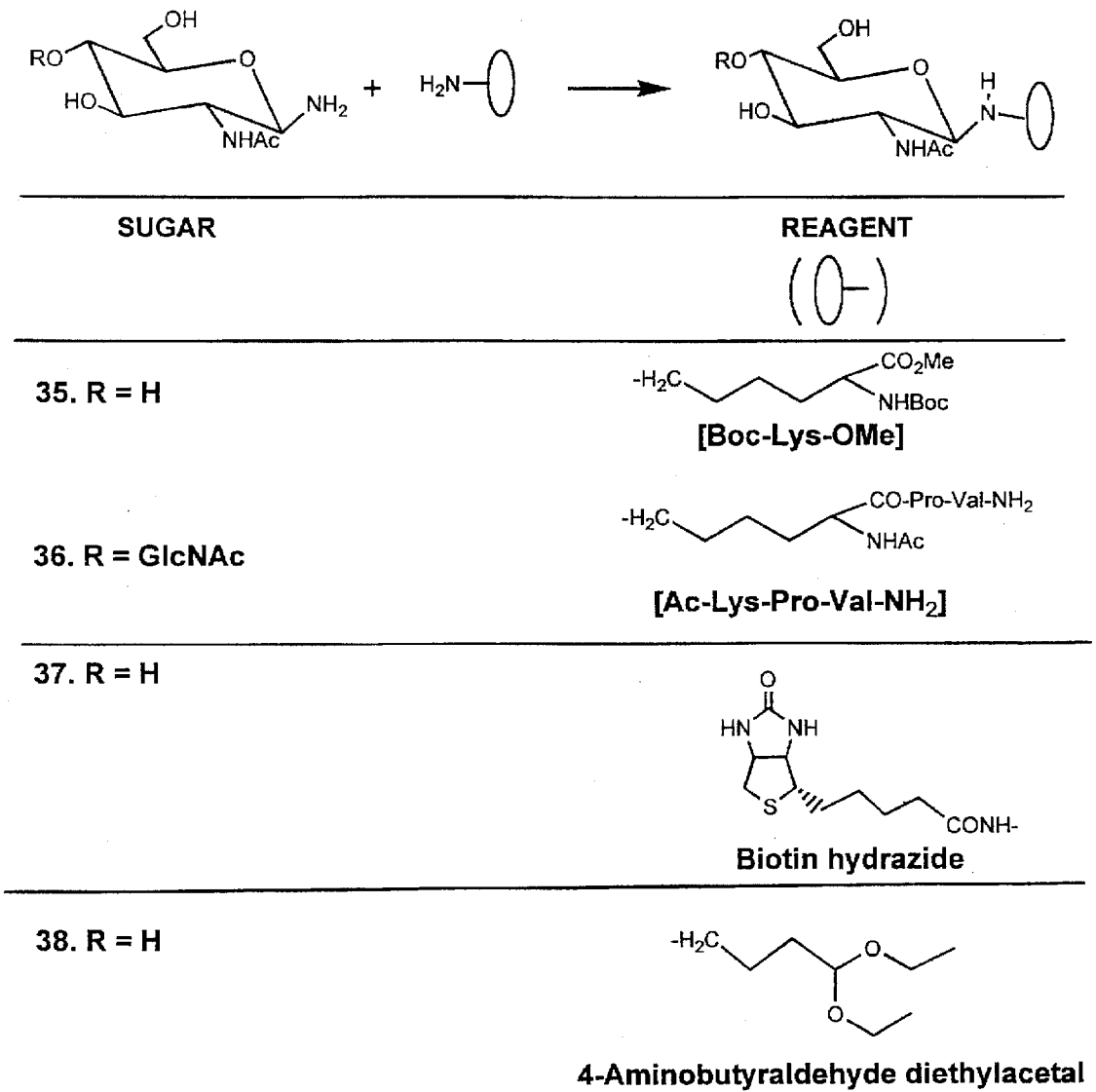
FIG. 11 is a reaction scheme showing the reaction of glycosyl-1-amines with the ε-amino group of lysine, biotin hydrazide and γ-aminobutyraldehyde diethyl acetal, respectively, in accordance with the present invention.

The conjugation of sugar residues, through their reducing end carbons, to the ε-NH$_2$ group of the lysine is demonstrated by the reaction of Boc-Lys-OMe acetate with 1-amino-1-deoxy-1,2-dideoxy-β-D-glucose (35), as shown in FIG. 11. The reaction was conducted as in Example 1.

Attachment of Sugar to Melanotropin C-terminal Peptide Analog

The glycosylamine of N,N'-diacetylchitobiose was conjugated to the ε-NH$_2$ group of lysine present in the peptide, Ac-Lys-Pro-Val-NH$_2$, as illustrated by reaction 36 (FIG. 11). The conjugate was prepared as in Example 1. This Example demonstrates the usefulness of the synthesis of neoglycopeptides in such studies and for biomedical and therapeutic applications including studies on the functional role of cell surface carbohydrates in cell-cell interactions.

The peptide itself is the acetylated C-terminal end of α-melanotropin which shows both antipyretic and anti-inflammatory effects (Deeter, L. B. et al *Peptides* 9:1285;1989; Hiltz, M. E. et al *Peptides* 12:767;1991). α-Melanotropin is a tridecapeptide hormone which is synthesized by the vertebrate pituitary (Hadley, M. E. et al *Science* 213:1025;1981). Recent studies implicate melanotropin in fetal development and in neural mechanisms related to learning memory. Introduction of glycan moieties as markers for recognition and active transport across membranes may have great potential for drug delivery in addition to increasing the lifetime of the active peptide by resisting proteolytic or other degradation. For example, enkephalin glycopeptides were found to rapidly cross the blood-brain barrier (Polt, R. et al *Glycoconjugate J* 10:261;1994). Macromolecular prodrugs incorporating carbohydrates have been used as recognition moieties. For example, polymer-drug-saccharide conjugates having peptidyl spacer arms have been reported (Duncan, R. et al *J Control Rel* 10:51;1989).

EXAMPLE 7

Synthesis of Biotinylated Oligosaccharide Conjugates

Avidin-biotin complexes are versatile tools for a number of bioanalytical applications including affinity purification, localization in tissues and the like (Wilchek, M. et al *Anal Biochem* 171:1;1988). Biotinyl glycans serve as tools for characterization of oligosaccharide-binding specificities (Shao, M. C. *Anal Biochem* 205:77;1992) and the regulation of glycan processing in glycoproteins (Shao, M. C. et al *J Biol Chem* 262:2973;1987) via the formation of stable multivalent complexes with avidin or streptavidin (Shao, M. C. et al *Methods Enzymol* 184:653;1990). Biotin hydrazide has been utilized for the direct biotinylation of carbohydrate groups on intact glycoproteins (Shannessy, D. J. et al *Anal Biochem* 163:204;1987).

A biotinylated saccharide conjugate 37, FIG. 11) was prepared by a transamination reaction of the present invention of biotin hydrazide with 1-amino-2-acetamido-1,2-dideoxy-β-D-glucopyranoside using the method of Example 1. The biotinylation reaction leaves the reducing end of the sugar intact and is therefore an excellent conjugate useful in studies aimed at exploiting avidin-biotin technology.

EXAMPLE 8

Synthesis of Drug-Oligosaccharide Conjugates

A number of commercially available drugs contain covalently attached sugar residues to their aglycone moieties e.g. glycoside antibiotics, cardiac glycoside etc. Frequently, the saccharide moieties are important for the proper functioning of the drug. Accordingly, there are significant applications for the synthesis of drugs conjugated to saccharide residues to increase the therapeutic and delivery potential and also for a better understanding about their uptake efficiency and pharmacokinetics. This is of particular value for therapeutics used to target cells and organs having carbohydrate-binding proteins/receptors. Carbohydrate ligands for selectins, by their ability to mediate a host of diseases have the potential to become anti-inflammatory drugs (Phillips, M. L. et al *Science* 250: 1130; 1990).

This Example illustrates the synthesis of oligosaccharide conjugates of two commercially available drugs, namely 1-hydrazinophthalazine (11, FIG. 2 and 21–24, FIG. 5) and isonicotinic hydrazide. 1-Hydrazinophthalazine is an antihypertensive drug, the major effects of which are on the cardiovascular system and is usually administered orally (*Physician's Desk Reference*, Medical Economics Dam Production Co. Montvale, N.J.; 809; 1994). Parenteral administration is done when the drug cannot be given orally or when there is an urgent need to lower blood pressure, for example to treat toxemia of pregnancy. Hydralazine is particularly useful in hypertensive disorders of pregnancy, which is one of the leading causes of maternal and fetal morbidity (Rakel, R. E. *Conn's Current Therapy* 244, 257, 260, 958; 1992).

Isonicotinic hydrazide is a commercially available drug, widely used as an antitubercular agent. Isonicotinic hydrazide-saccharide conjugates were prepared by the reaction of isonicotinic hydrazide with glycosyl-1-amine derivatives of N-acetylglucosamine (13, FIG. 2) and maltotriose respectively.

The ease with which these two drugs react with glycosyl-1-amines and the high yields are the main attractive features associated with the preparation of these two drug-saccharide conjugates. The immense therapeutic and commercial value of the above two drugs and the potential gains emanating from the studies involving their saccharide conjugates, as they relate to delivery, biodistribution, pharmacokinetics and potency are other attractive features.

EXAMPLE 9

Synthesis of Oligosaccharide Conjugates with a Linker/Spacer Group

The reaction of 1-amino derivative of N-acetylglucosamine with γ-aminobutyraldehydediethylacetal afforded a product (reaction product 38, FIG. 9) that is useful (i) for the introduction of a spacer arm consisting of four carbon atoms; and (ii) to introduce an aldehyde function, protected as its acetal derivative, at the other end. Spacer arms are frequently employed in coupling reactions to avoid steric and other undesirable interactions. The aim of the glycoconjugate generated by reacting with γ-aminobutyraldehydediethylacetal is to take advantage of both of the above features while generating glycoconjugate probes. A method for attaching an aldehyde function to polysaccharides has been reported, by the alkylation of the latter with chloroacetaldehyde dimethyl acetal (Bogwald, J. et al *Carbohydr Res* 148:101;1986). Deacetalization of the product gave a polysaccharide with aldehyde function useful to conjugate other groups, for example, proteins.

We claim:

1. A method for the synthesis of an N-linked glycoconjugate comprising the single step of reacting a glycosyl-1-amine with a nucleophilic reagent, at conditions which favor nucleophilic substitution, to effect nucleophilic substitution of the 1-amino functional group of the glycosyl-1-amine.

2. A method according to claim 1, wherein the nucleophilic reagent has an —NH$_2$ or —NHNH$_2$ group.

3. A method according to claim 2, wherein the nucleophilic reagent is isonicotinic hydrazide.

4. A method according to claim 2, wherein the nucleophilic reagent is a compound having a linker/spacer group.

5. A method according to claim 4, wherein the compound having a linker/spacer group is γ-aminobutyraldehydediethylacetal or 1-N-(9-fluoromethoxycarbonyl)-6-diamino-hexane.

6. A method according to claim 2, wherein the ratio of glycosyl-1-amine to nucleophilic reagent is in the range of from about 1:1 to about 1:2 by weight.

7. A method according to claim 6, wherein the reaction is conducted in the presence of an aprotic solvent.

8. A method according to claim 7, wherein the aprotic solvent is selected from the group consisting of pyridine, DMSO and DMF.

9. A method according to claim 7, wherein the reaction temperature is 50° C.

10. A method according to claim 2, wherein the glycosyl-1-amine is 1-amino-1-deoxy-maltooligosaccharide.

11. A method according to claim 2, wherein the glycosyl-1-amine is selected from a monosaccharide with a reducing end, and an oligosaccharide having a reducing end monosaccharide.

12. A method according to claim 2, wherein the nucleophilic reagent is dansyl hydrazine.

13. A method according to claim 1, wherein the nucleophilic reagent is a chromophore or fluorophore.

14. A method according to claim 13, wherein the chromophore or fluorophore is selected from the group consisting of substituted aliphatic and aromatic amines, hydrazines and benzylamines.

15. A method according to claim 14, wherein the chromophore or fluorophore is selected from the group consisting of dansyl hydrazine, 1-hydrazinophthalazine, 9-fluorenamine, isonicotinic hydrazide, isonicotinic hydrazide, 2-hydrazinopyridine and 4-amino-4'-dimethylaminoazobenzene.

16. A method according to claim 1, wherein the nucleophilic reagent is a compound having a chemiluminescent group.

17. A method according to claim 16, wherein the compound having a chemiluminescent group is selected from the group consisting of luminols and analogs thereof.

18. A method according to claim 17, wherein the compound having a chemiluminescent group is N-(4-aminobutyl)-N-ethylisoluminol.

19. A method according to claim 1, wherein the nucleophilic reagent is a compound having a biotin group.

20. A method according to claim 1, wherein the nucleophilic reagent is a lipid.

21. A method according to claim 20, wherein the lipid is selected from the group consisting of dipalmitoylphosphatidylethanolamine, dihexadecylglycerophosphoethanolamine, n-tetradecylamine, n-octylamine and cylcohexylamine.

22. A method according to claim 1, wherein the nucleophilic reagent is selected from the group consisting of biotin hydrazide and peptides containing lysine groups.

23. A method according to claim 22, wherein the peptide is selected from the group consisting of L-lysyllysine and tert-butyloxycarbonyl-Lys-OMe.

* * * * *